United States Patent [19]

Buchman et al.

[11] Patent Number: 5,567,736
[45] Date of Patent: Oct. 22, 1996

[54] USE OF A CHOLINE SALT TO INHIBIT FATTY LIVER IN PATIENTS RECEIVING TOTAL PARENTERAL NUTRITION

[76] Inventors: Alan L. Buchman, 1280 W. Peachtree St., Atlanta, Ga. 30309; Donald J. Jenden, 3814 Castlerock Rd., Malibu, Calif. 90265; Marvin E. Ament, 291 S. Glenroy, Los Angeles, Calif. 90049; Kenneth Breslow, 3651 Meier St., Los Angeles, Calif. 90066; Mark D. Dubin, 1609 S. Veteran Ave. #1, Los Angeles, Calif. 90024

[21] Appl. No.: 301,042

[22] Filed: Sep. 6, 1994

Related U.S. Application Data

[63] Continuation of Ser. No. 970,086, Nov. 2, 1992, abandoned.

[51] Int. Cl.$^6$ ............................................. A61K 31/14
[52] U.S. Cl. ............................................. 514/642
[58] Field of Search ............................................. 514/642

[56] References Cited

U.S. PATENT DOCUMENTS

| | | | |
|---|---|---|---|
| 4,460,601 | 7/1984 | Picciola et al. | 424/300 |
| 4,626,527 | 12/1986 | Wurtman et al. | 514/78 |
| 5,001,117 | 3/1991 | Hirsch | 514/78 |

FOREIGN PATENT DOCUMENTS

| | | |
|---|---|---|
| 2215 | 11/1962 | France . |
| 2896 | 8/1963 | France . |
| 5060 | 12/1965 | France . |
| 3721137 | 6/1987 | Germany . |
| 63-208524 | 8/1988 | Japan . |
| 63-233800 | 9/1988 | Japan . |
| 1-141572 | 6/1989 | Japan . |
| WO91/09590 | 7/1991 | WIPO . |

OTHER PUBLICATIONS

Zeisel, Steven H., "Modern Nutrition in Health & Disease", (Shields & Young), 1988, pp. 440–445.
Zeisel, Steven H., "Choline: An Important Nutrient in Brain Development, Liver Function and Carcinogenesis", Journal of the American College Nutrition, vol. 11, No. 5, pp. 473–481 (1992).
Buchman, Alan L.; Dubin, M.; Jenden D.; Moukarzel, A.; Roch, M. H.; Rice, K.; Gornbein, J.; Ament, M. E.; and Eckhert; "Lecithin Increases Plasma Free Choline and Decreases Hepatic Steatosis in Long–Term Total Parenteral Nutrition Patients," Gastroenterology 1992; 102:pp. 1363–1370.
F. Magrassi, Trattato Di Medicina Interna, 1981, pp. 260–279.
The Clinical Studies of The Effect of CDP–choline on a Post Operative Hypoxemia, pp. 876–881, 1973.
Achord, "Malnutrition and the Role of Nutritional Support in Alcoholic Liver Disease," 82 Am. J. Gastroenterology 1–7 (1987).
Agut et al., "Dissimilar Effects in Acute Toxicity Studies of DCP–Choline and Choline," 33 Drug Res. 1016–1017 (1983).

Balistreri et al., "Total parenteral nutrition–associated cholestasis: factors responsible for the decreasing incidence," in Falk Symposium 63, Paediatric Cholestasis 191–204 (1992).
Bowyer et al., "Plasma carnitine levels in patients receiving home parenteral nutrition," 43 Am. J. Clin. Nutr. 85–91 (1986).
Brown et al., "Total Nutrient Admixture: A Review," 10 J. Parenteral and Enteral Nutr. 650–658 (1986).
Ciaceri, "Toxicological Studies on CDP choline," in Zappia et al., Novel Biochemical, Pharmocological and Clinical Aspects of Cytidinephosphocholine 159–167 (1985).
Chawla et al., "Choline May Be and Essential Nutrient in Malnourished Patients With Cirrhosis," 97 Gastroenterology 1514–1520 (1989).
Conlay et al., "Decreased Plasma Choline Concentrations in Marathon Runners," Letter to the Editor at 892, The New England Journal of Medicine (Oct. 2, 1986).
Davis et al., "Increased plasma carnitine in trauma patients given lipid–supplemented total parenteral nutrition," 48 Am. J. Clin. Nutr. 1400–1402 (1989).
Drongowski et al., "An Analysis of Factors Contributing to the Development of Total Parenteral Nutrition–Induced Cholestasis," 13 J. Parenteral And Enteral Nutr. 586–589 (1989).
Fischer, "Editorial: Abnormalities of Liver Function and Hepatic Damage Associated with Total Parenteral Nutrition," 7 Nutrition 5–6 (1991).
Freund et al., "Early Quantitative and Qualitative Changes in Liver Lipids During Total Parenteral Nutrition," 6 Nutrition 119 (1990).
Freund, "Abnormalities of Liver Function and Hepatic Damage Associated with Total Parenteral Nutrition," 7 Nutrition 1–4 (1991).
Galambos et al., "Relationship Between 505 Paired Liver Tests and Biopsies in 242 Obese Patients," 74 Gasteroenterology 1191–1195 (1978).
Garnier–Chevereau et al., "Hepatobiliary modifications associated with TPN in rats: influence of different components of lipid emulsions," 10 Thirteenth ESPEN Congress, Sep. 1–4, 1991, Artwerp, Belgium, Supplement 47.
Ho et al., "Toxic Interaction between Choline and Morphine," 51 Toxicology and Applied Pharmacology 203–208 (1979).
Hodge et al., "The Acute Toxicity of Choline Hydrochloride in Mice and Rats," 5 Proc. Soc. Exp. Biol. 281–282 (1942).
Hunt, "Some Physiological Actions of the Homocholines and of Some of Their Derivatives," 6 J. Pharm. Exp. Ther 477–525 (1914).
Johnston, "The Toxic Effects of Amines," 42 J.I.D. 473–484 (1928).

(List continued on next page.)

*Primary Examiner*—Marianne M. Cintins
*Assistant Examiner*—William R. A. Jarvis
*Attorney, Agent, or Firm*—Brinks Hofer Gilson & Lione

[57] ABSTRACT

Choline is added as a supplement to nutrient solutions used in total parenteral nutrition. Addition of choline to the TPN solution maintains plasma-free choline levels within normal limits and inhibits fatty liver.

3 Claims, No Drawings

OTHER PUBLICATIONS

Langrehr et al., "Hepatic Steatosis due to Total Parenteral Nutrition: The Influence of Short–Gut Syndrome, Refeeding, and Small Bowel Transpiration," *50 J. Surgical Research* 335–343 (1991).

Lemann et al., 4th UEGW Berlin at A84 (1995).

McDonald et al., "Reversal of Fatty Liver by Intralipid in Patients on Total Parenteral Alimentation," *64 Gastroenterology* 885 (1973).

Merritt, "Cholestais Associated with Total Parenteral Nutrition," *22 J. Pediatric Gastroenterology and Nutrition* 9–22 (1986).

Nakagawa, "Effect of Various Lipid Emulsions on Total Parenteral Nutrition Induced Hepatosteatosis in Rats." *J. Parenteral and Enteral Nutrition* 137–142 (1991).

Noussbaum et al., "Pathogenesis of Hepatic Steatosis During Total Parenteral Nutrition," *in Nyhus, 23 Surgery Annual* 1–11 (1991).

Neuman et al., "Acute Toxicity of Choline chloride Administered Orally to Rats," *53 Proc. Soci. Exp. biol.* 87–88 (1945).

Niemiec et al., "Compatibility considerations in parenteral nutrient solutions," *41 Am. J. Hosp. Pharm.* 893–911 (1984).

Pertkiewicz et al., "TPN Associated Liver Dysfunction –Significance of Composition and Contamination of Amino Acid Solution," *8 Clin. Nutr. Supp.* 91 (1989).

Quigley et al., "Hepatobiliary Complications of Total Parenteral Nutrition," *104 Gastroenterology* 286–301 (1993).

Sahu et al., "Effect of Chronic Choline Administration in Rats," *24 Indian J. of Experimental Biology* (1986).

Saville et al., "Choline–Induced Pyridoxine Deficiency in Brolier Chickens," *43 Australian Veterinary J.* 346–348 (1967).

Sax et al., "Hepatic Steatosis in total parenteral nutrition: Failure of fatty infiltration to correlate with abnormal serum hepatic enzyme levels," *100 Surgery* 697–703 (1986).

Shaul et al., "Liver Abnormalities in Patients Receiving TPN Are Not Correlated With TPN Composition," *in 13 SPEN 17S* (1989).

Shills et al., "Hepatic Dysfunction," *in 2 Modern Nutrition in Health and Disease* 1057–1058 (7th Ed. 1988).

Tamminga et al., "Depression Assiociated With Oral Choline" *The Lancet,* 905 (Oct. 23, 1976).

Wagner et al, "Similar Liver Function Abnormalities Occur in Patients Receiving Glucose–Based and Lipid Based Parenteral Nutrition," *78 Am. J. Gastroenterology* 199–200 (1983).

Wang et al., "A simple, sensitive, and specific assay for free choline in plasma," *63 Anal. Biochem.* 195–201 (1975).

Whalen et al., "A Proposed Cause for the Hepatic Dysfunction Association With Parenteral Nutrition," *25 J. Pediatric Surgery* 622–626 (1990).

Wurtman et al., "Lecithin Consumption Raises Serum–Free–Choline Levels," *in The Lancet* 68–69 (Jul. 9, 1977).

Yao et al., "The Active Synthesis of Phosphatidylcholine Is Required for Very Low Density Lipoprotein Secretion from Rat Hepatocytes," *263 J. Biological Chem.* 2998–3004 (1988).

Zakim et al., "Hepatic Dysfunction During Total Parenteral Nutrition," *in 2 Hepatology: A Textbook of Liver Disease* 1429 (1990).

Zeisel, "Dietary choline: Biochemistry, physiology, and pharmacology," *Ann. Rev. Nutr.* 95–121 (1981).

Kaminski, D; Adams, A; and Jellinek, M: The Effect of Hyperalimentation of Hepatic Lipid Content and Lipogenic Enzyme Activity in Rats and Man; Surgery (Jul. 1980) pp. 93–100.

Burt, ME; Hanin, I; Brennan, MF: Choline Deficiency Assoiciated With Total Parenteral Nutrition; The Lancet, Sep. 20, 1980 pp. 638–639.

Chawla, RK; Berry, CJ; Kutner, MH; and Rudman, D: Plasma Concentrations of Transsulfuration Pathway Products During Nasoenteral and Intravenous Hyperalimentation of Malnourished Patients[1–3]; The Amer. Jour. of Clin. Nutrition 42: Oct. 1985, pp. 577–584.

Hall, RI; Ross, LH; Bozovic, MG and Grant, JP: The Effect of Choline Supplementation on Hepatic Steatosis in the Parenterally Fed Rat; Journ. of Parenteral and Enteral Nutrition, vol. 9, No. 5, pp. 597–599, 1985.

Sheard, NF; Tayek, JA; Bistrian, BR; Blackburn, GL; Zeisel, SH: Plasma Choline Concentration in Humans fed Parenterally, The Amer. Jour of Clinical Nutrition 43: Feb. 1986, pp. 219–224.

USE OF A CHOLINE SALT TO INHIBIT FATTY LIVER IN PATIENTS RECEIVING TOTAL PARENTERAL NUTRITION

This application is a continuation of U.S. patent application Ser. No. 07/970,086, filed Nov. 2, 1992, now abandoned.

BACKGROUND OF THE INVENTION

1. Field of the Invention:

The present invention relates generally to techniques for meeting a patient's nutritional needs by intravenous feedings. More particularly, the present invention relates to the nutrient solutions which are used in such intravenous feeding techniques.

2. Description of Related Art:

Total parenteral nutrition (TPN) involves satisfying a patient's nutritional needs by means of intravenous feedings. TPN, which sometimes is also referred to as hyperalimentation, provides all of the carbohydrates, proteins, fats, water, electrolytes, vitamins and minerals needed for the building of tissue, expenditure of energy and other physiologic activities.

TPN originated as an emergency procedure which was first used following surgery for severe and massive trauma of the gastrointestinal tract. TPN has become a relatively common means of providing bowel rest and nutrition in a variety of conditions. Although TPN was initially employed as a short-term temporary nutrition procedure, it has also become widely used as a long-term nutrition protocol.

Parenteral nutrition, whether it be total or supplemental, has been employed in a wide variety of chronic conditions. For example, patients suffering malnutrition from acute and chronic inflammatory bowel diseases many times require total parenteral nutrition. In addition, patients suffering from partial or total obstruction of the gastrointestinal tract that cannot be relieved immediately by surgery are also candidates for TPN. Other patients who receive TPN are those suffering from massive burns that produce critical protein loss and those patients suffering from other disorders in which malnutrition is a threat to their life and they cannot receive or absorb nutrients via the digestive tract.

The nutrient solution or mix which is administered intravenously to the patient during TPN is generally tailored to the individual needs and tolerance of the patient. In general, the nutrient solution is an aqueous solution containing dextrose, amino acids, electrolytes, trace elements and vitamins. Two to three liters of the nutrient solution is administered intravenously to the patient during total parenteral nutrition. Administration of the nutrient solution is generally accomplished by way of a central venous catheter which is inserted in the superior vena cava.

Although total parenteral nutrition is a lifesaving feeding program for many patients, there are a number of complications which may develop. In addition, the patient may suffer adverse reactions due to sensitivity to some of the elements in the nutrient mix and the possibility of infections always exists. Other complications that may develop include phlebitis and thrombosis of the vena cava, electrolyte imbalance, hyperglycemia, cardiac overload, dehydration, metabolic acidosis, mechanical trauma to the heart, metabolic bone disease and renal diseases.

In addition to the above noted possible complications, it has been noted that patients receiving long term parenteral nutrition tend to develop choline deficiency as evidenced by low plasma choline levels. The choline deficiency many times is manifested as hepatic steatosis. It would be desirable to provide a simple and effective treatment which is capable of increasing plasma-free choline levels in patients receiving total parenteral nutrition. Further, it would be desirable to provide a treatment which is effective in reducing hepatic steatosis and other complications which are associated with choline deficiency resulting from long-term total parenteral nutrition.

SUMMARY OF THE INVENTION

In accordance with the present invention, it was discovered that plasma-free choline levels in patients receiving total parenteral nutrition can be increased to normal levels and/or maintained at normal levels by including choline in the nutrient solution which is administered to the patient. Inclusion of choline in the nutrient solution not only maintains plasma free choline levels in normal ranges, but also is effective in treating and preventing hepatic steatosis.

In accordance with the present invention, choline in the form of choline chloride or other choline salt is added to the nutrient solution which is normally administered to the patient receiving total parenteral nutrition. The normal dosage of nutrient solution administered to the patient on a daily basis is on the order of two to three liters of solution. As a feature of the present invention, choline chloride or other choline salt is added to the nutrient solution in an amount sufficient to provide from 0.25 to about 8 grams of choline per liter of solution.

It was discovered that the above concentrations of choline in the nutrient solution are tolerated well by patients and provide a daily dosage of choline which is effective in maintaining plasma free choline levels within normal ranges during chronic total protein nutrition therapy. In addition, it was discovered that addition of choline to the nutrient solution at the preceding dosage levels is effective in decreasing and eliminating hepatic steatosis in those patients suffering from chronic choline deficiency.

As a feature of the present invention, an improved nutrient solution is provided by adding sufficient choline chloride or other salt of choline to the TPN patient's normal nutrient solution. No complicated formulation procedures or difficult mixing steps are necessary to carry out the present invention. The desired dosage of choline chloride or other salt of choline is added to the aqueous nutrient solution with the choline enriched solution being administered to the TPN patient in accordance with normal practice.

Choline chloride does not react with or otherwise adversely affect the dextrose, amino acids, electrolytes, trace elements, vitamins and other compounds typically found in total parenteral nutrient solutions. In addition, choline is relatively stable within the nutrient solution when stored under normal conditions. The choline does not deteriorate or otherwise lose its potency over relatively long periods of time. As a result, choline may be added to the TPN nutrient solution by the pharmacist or it can be added by the patient immediately prior to administration of the solution. The use of choline as a supplement to TPN nutrient solutions is easily incorporated into situations requiring both long-term and short-term total parenteral nutrition.

The above-discussed and many other features and attendant advantages of the present invention will become better understood by reference to the detailed description when taken in conjunction with the accompanying drawings.

DESCRIPTION OF THE PREFERRED EMBODIMENTS

The nutrient solutions which are used in feeding patients by total parenteral nutrition (TPN) are well known. The particular ingredients which are included in the nutrient solution vary widely depending upon patient nutritional needs and the patient's medical condition. Generally, the most prevalent ingredient in nutrient solutions is dextrose with lesser amounts of amino acids, electrolytes, trace elements and vitamins being included. In general, the nutrient solution will include 10–35 volume percent of a dextrose solution. Dextrose solutions are aqueous-based solutions which contain between 10 and 35 grams of dextrose per liter of solution. Such dextrose solutions are commercially available from Abbott Laboratories, Baxter Healthcare Corp., McGaw Laboratories and others.

Nutrient solutions also typically include from 2–5 weight percent of amino acids. The amino acids used in the nutrient solution can be any of the essential amino acids and can be included in a variety of concentrations and mixtures. Preferred amino acids for use in nutrient solutions include threonine, serine, proline, glycine, alanine, valine, methionine, isoleucine, leucine, tyrosine, phenylalanine, tryptophan, lysine, histidine and arginine. In addition to dextrose and amino acids, most nutrient solutions include electrolytes such as potassium, sodium, chloride, magnesium, acetate, calcium, and phosphorous and others. These electrolytes are generally included in relatively small amounts on the order of 1 percent or less.

Trace elements and vitamins are also included in most nutrient solutions. Typical trace elements include selenium, chromium, manganese, zinc and others. Vitamins which are usually included in nutrient solutions include A, $B_1$, $B_2$, $B_6$, $B_{12}$, C, D, E, biotin, pantothenic acid, etc. Trace elements are usually present in concentrations on the order of less than one-tenth of one percent. Vitamins are generally present in amounts sufficient to meet daily vitamin requirements which have been established and are widely known.

In accordance with the present invention, choline chloride or another choline salt is added to the nutrient solution to provide for direct intravenous introduction of choline into the patient. Although choline chloride is the preferred form of choline which is added to the nutrient solution, other choline salts such as choline bitartrate, choline dihydrogen citrate, choline phosphate and choline bicarbonate may be used. In addition, choline precursors and choline metabolites such as phosphatidyl choline, CDP-choline, soy lecithin, etc., may be used. For the purposes of this specification and the appended claims, the term "choline" when used to identify the ingredients added to or present in a nutrient solution is intended to include choline salts, choline precursors and choline metabolites wherein the choline precursors or choline metabolites are capable of being converted into choline when mixed with the TPN solution or introduced in vivo.

The amount of choline or choline salt which is added to the nutrient solution may be varied depending upon the patient's plasma-free choline level, the degree of hepatic steatosis and the severity of other medical problems associated with choline deficiency.

In general, it is preferred that the amount of choline chloride or choline salt which is added to the nutrient solution be sufficient to provide a choline concentration in the solution of from about 0.25 to about 8 grams choline per liter of solution. This concentration of choline provides an acceptable daily dosage level of choline when the patient receives from 2 to 3 liters of the nutrient solution each day. The desired total daily choline dosage should be on the order of between 0.5 to 8 grams of choline.

Administration of the nutrient solution parenterally into the patient is accomplished by well established techniques for administration of nutrient solutions for total parenteral nutrition. The total amount of nutrient solution may be administered as separate aliquots at different times during the day. However, it is preferred that the two to three liter dose of nutrient solution be administered each evening over a six to ten hour period, or on a continuous 24 hour basis.

The choline chloride or other choline salt which is added to the nutrient solution is preferably not added directly in solid form. Instead, it is preferred that the appropriate amount of choline salt be weighed and dissolved in sterile water for injection USP to form an approximately 50% by weight solution of choline salt. The resulting choline solution is then passed through a 0.2 μm pore size sterilizing filter and packaged in sterile vials. Suitable filters for filtering the choline solution include 0.2 μm Nylon 66 sterilizing filter cartridges such as those manufactured by Pall Ultrafine Corp. (Glen Cove, N.Y.). Other Nylon filters may be used as well as filters made from other materials, such as cellulose acetate and polysulfone.

Prior to use, the appropriate amount of choline solution is transferred from the sterile vial and is added to the nutrient solution which typically is contained in a TPN bag. Choline chloride was found to be stable in various TPN nutrient solutions for at least 30 days and there were no adverse affects on the TPN solution turbidity, pH, or amino acid concentrations.

It is preferred that the aqueous solution of choline be stored separate from the TPN solution and added to the nutrient solution on the day the solution is to be prepared. The concentration of choline within the nutrient solution may be varied depending upon the total amount of solution being administered. Preferably, the amount of choline solution added to the nutrient solution administered to the patient should provide a total daily dosage of choline of between about 0.5 to 8 grams of choline. Total daily dosages on the order of 1–6 grams of choline will be adequate for most treatment regimens.

Examples of practice are as follows:

Four subjects who were known to have low plasma free choline levels and hepatic steatosis were studied. The subjects included 3 females aged 45, 50 and 72 years and 1 male aged 43 years. Two subjects had short bowel syndrome from Crohn's disease, one had radiation enteritis and the fourth had pseudo-obstruction. The subjects had received home TPN for 9.7±4.7 years. Their TPN consisted of 2–3L of 15–25% dextrose solution with 3.0–3.5% amino acids, electrolytes, trace elements and vitamins. All subjects received 19.5±3.7 kcal-kg day actual body weight (range 16–24 kcal/kg/d). This level of support varied between subjects depending upon individual variation in oral intake and intestinal absorption.

Intravenous lipid (Intralipid 20%, Clintec, Deerfield, Ill.) supplied 42.5%±25.7% of daily intravenous caloric intake. No adjustments in TPN ingredients were made during the study except with respect to the addition of choline chloride. The TPN solution for each subject included 2.3–5 g of methionine on a daily basis depending upon the total amino acid concentration. The vitamin preparation included 5 μg vitamin B12 and 400 μg folate on a daily basis. All subjects received their TPN nightly as one dose over a period of 10–12 hours.

The subjects were supplied with 42 single-dose vials containing 8 g choline chloride dissolved in 16 ml of water for injection USP. The subjects were prescribed 1, 3 or 4 g of choline chloride as a total dose in the TPN solution each night. The subjects withdrew into a syringe the appropriate amount of choline chloride each night and injected it into their TPN bag. Choline chloride in concentrations as high as 10 g/l is stable for at least 30 days and does not affect the pH or amino acid availability of the TPN solution.

The subjects were seen at baseline, weekly for 6 weeks during the choline infusion, and again 4 weeks following the discontinuation of the choline-supplemented TPN. Plasma-free choline level, serum SGOT, SGPT and total cholesterol levels were measured at each visit. Plasma free choline was measured by gas chromatography and mass spectrophotometry (See Jenden DJ, Roch M, Booth RA. Simultaneous measurements of endogenous and deuterium-labeled tracer variants of choline and acetylcholine in subpicomole quantities by gas chromatography spectrometry. Anal Biochem. 55:438–48, 1973; and Freeman JJ, Choi RL, Jenden DJ. Plasma choline: its turnover and exchange with brain choline. J. Neurochem. 24:729–34, 1975.)

The hepatic transaminase levels and cholesterol were determined using standard automated techniques. Plasma phospholipid bound choline was measured at baseline, at the end of the 6 week nightly choline infusion and 4 weeks later following extraction as described by Folch et al (Folch J, Lees M, Stanley GHS. A simple method for the isolation and purification of total lipids from animal tissue. J. Bio Chem. 226:497–509, 1957.) and hydrolysis as described by Jope and Jenden (Jope RS, Jenden DJ. Choline and phospholipid metabolism and the synthesis of acetylcholine in rat brain. J. Neurosci Res. 4:69–82, 1979.). All blood samples were obtained on the subjects following an overnight fast and 3–5 hours following completion of the TPN.

Computed tomography (CT) was used as a non-invasive method for quantifying hepatic fat density. Limited non-contrast CT scanning of the liver and spleen was performed using a GE 9800 CT scanner (Milwaukee, Wis.). Multiple contiguous 1-cm axial sections at 1-cm intervals were obtained. Attenuation values for regions of interest in the liver and spleen were generated from multiple representative sections. An average (mean) CT number in Hounsfield units (HU) was then calculated for each organ. Liver density was determined using two currently acceptable methods: a) the average absolute liver CT number, and b) the liver-spleen differential obtained by subtracting the average spleen CT number from the average liver CT number (to correct for interscan variability).

In the normal state, the liver and spleen maintain a fairly constant relationship in terms of relative CT numbers on non-contrast scans. On the main scanner employed at our institution, normal liver density corresponds to approximately 45 HU in absolute terms, and normal liver attenuation values exceed those of the spleen by approximately 8 HU (i.e., a liver-spleen differential of approximately positive 8 HU). Fat has a distinctly lower attenuation than other tissues and thus a distinct appearance on the CT image, as well as a distinctly low CT number in HU. Hepatic density and hepatic steatosis are therefore inversely related. Fatty liver was defined as an absolute CT number </=45 HU, or a liver-spleen differential of </= positive 8.0 HU (with 0-to-positive 8 HU representing borderline fatty change and </=0 HU corresponding to marked fatty infiltration).

All 4 subjects had low plasma free choline levels at the beginning of the study (5.2±2.1, range 2.7–7.2 normal 11.4±3.7 nmol/ml). The full 10-week study was completed by all 4 subjects. One subject (#4) mistakenly received a CT scan at 5 weeks and therefore believing that to be the end of the study, did not infuse choline with her TPN during the 6th week. This same subject also required two dose adjustments in the choline chloride because of mild nausea occurring upon awakening in the morning at the end of the choline infusion. Her dose was decreased from 2 g/day to 1 g/day on day 10, and then to 1 gm every other day on day 24 until increased back to 1 g/day on day 30 without complaints for the remainder of the study. The weekly choline levels for each subject are shown in Table 1.

TABLE 1

| | Liver-spleen Hounsfield unit differential | | | | |
|---|---|---|---|---|---|
| | Baseline | 2 Wks | 4 Wks | 6 Wks | 4 Wks post choline |
| Subject 1 | −47.0 | −3.9 | −3.8 | 3.3 | 10.6 |
| Subject 2 | −0.7 | 19.8 | 19.2 | 15.4 | 15.7 |
| Subject 3 | 0.3 | 13.2 | 17.2 | 20.8 | 15.0 |
| Subject 4 | −9.4 | 4.5 | 5.6 | 12.8 | (−6.3)* |

*10 weeks post choline supplementation

During the pharmacokinetic studies preceding the 6 week choline infusion study, Subject #4 tolerated plasma free choline levels as high as 230 nmol/ml without any side effects. Because this subject had a history of early morning headaches which were at one time associated with lipid emulsion, it is unclear whether the choline was responsible. No other subject experienced any side effects or required a dose adjustment.

The plasma free choline level increased into the normal range (normal 11.4+/−3.7 nmol/ml) in all subjects after one week of choline supplementation. Hepatic steatosis decreased significantly in all 4 subjects at the time of the initial CT scan, which was obtained two weeks after choline supplementation was initiated (Table 1). This was demonstrated by a marked increase in liver density. The CT number difference yielded by the liver-spleen subtraction method improved by an average 20+/−16.5 HU (−14.2+/−22.3 HU to 8.4 +/−10.3 HU, p=0.002. Hepatic steatosis continued to decrease during the six weeks of choline supplementation, and completely resolved in all four subjects. The liver-spleen CT number differential assumed a normal or near-normal relationship on the concurrent scans. Although plasma free choline levels were similar to their baseline values four weeks after choline was discontinued, hepatic steatosis had not yet returned to baseline on the follow-up post-supplementation CT.

Because of missed appointments, subject #3 was followed up ten weeks after the six weeks of choline supplemented TPN had been discontinued. Her hepatic steatosis had recurred. Liver density appeared identical to the baseline CT scan, and the liver-spleen differential returned to its original, pre-choline supplementation value.

No significant decreases in the hepatic transaminase levels were noted during the study; except for Subject #1 who also had the most significant hepatic steatosis and decrease in hepatic steatosis. Three of the four subjects had normal AST and ALT at baseline. No change in total serum cholesterol was noted during the study.

As is apparent from the preceding study, the choline supplementation of TPN nutrient solutions provided in accordance with the present invention is effective in increasing the plasma-free choline levels in long-term TPN patients. Further, the choline supplementation in accordance with the present invention is effective in reducing hepatic steatosis which is associated with long-term TPN.

Although the preceding description has focused mainly on administering choline via a TPN solution, the present invention also contemplates the administration of choline intravenously to treat a variety of patients who are suffering from choline deficiency. Such patients include those who are not receiving TPN. The choline is administered using a pharmaceutically suitable carrier with dosages being in the same range as for TPN supplementation previously described. The dose may be varied depending upon the degree of choline deficiency and response to therapy. Dosage levels may be reduced as levels of choline in the patients blood reach normal levels and reversal of any end-organ damage caused by the choline deficiency occurs.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A method for inhibiting fatty liver in a human patient receiving total parenteral nutrition, comprising administering a nutrient solution to the patient parenterally, wherein the nutrient solution comprises a choline salt and wherein the nutrient solution is administered in an amount sufficient to increase plasma free choline to at least a normal level.

2. The method according to claim 1 wherein said nutrient solution contains about 0.25 to about 8 grams of choline salt per liter of solution.

3. The method according to claim 1 wherein said choline salt in said nutrient solution is in the form of choline chloride.

* * * * *

UNITED STATES PATENT AND TRADEMARK OFFICE
CERTIFICATE OF CORRECTION

PATENT NO. : 5,567,736
DATED : October 22, 1996
INVENTOR(S) : Buchman et al.

Page 1 of 2

It is certified that error appears in the above-identified patent and that said Letters Patent is hereby corrected as shown below:

In the Title Page

In column 1, line 5, under "OTHER PUBLICATIONS", replace "vol." with --Vol.--.

In column 1, line 6, under "OTHER PUBLICATIONS", immediately after "Jenden" insert --,--.

In column 2, line 13, under "OTHER PUBLICATIONS", replace "and" with --an--.

In column 2, line 21, under "OTHER PUBLICATIONS", replace "(1989)" with --(1988)--.

In column 1, line 13, before "*J.*" insert --15--.

In column 1, line 15, replace "Noussbaum" with --Nussbaum--.

In column 1, line 32, replace "Brolier" with --Broiler--.

In column 2, line 1, replace "Assiociated" with --Associated--.

In column 2, line 22, before "*Ann.*" insert --1--.

UNITED STATES PATENT AND TRADEMARK OFFICE
CERTIFICATE OF CORRECTION

PATENT NO.   : 5,567,736
DATED        : October 22, 1996
INVENTOR(S)  : Buchman et al.

Page 2 of 2

It is certified that error appears in the above-identified patent and that said Letters Patent is hereby corrected as shown below:

In column 2, line 28, replace "Assiociated" with --Associated--.

In column 2, line 38, replace "vol." with --Vol.--.

Signed and Sealed this

Second Day of June, 1998

Attest:

BRUCE LEHMAN

Attesting Officer

Commissioner of Patents and Trademarks